United States Patent [19]

Nakae et al.

[11] Patent Number: 4,560,665

[45] Date of Patent: Dec. 24, 1985

[54] METHOD OF MEASURING MEMBRANE FUSION

[75] Inventors: Taiji Nakae, Kanagawa; Eisaku Ryo, Isehara, both of Japan

[73] Assignee: Fujirebio Kabushiki Kaisha, Kanagawa, Japan

[21] Appl. No.: 613,893

[22] Filed: May 24, 1984

[30] Foreign Application Priority Data

May 27, 1983 [JP] Japan .................................. 58-92489

[51] Int. Cl.$^4$ ...................... G01N 21/77; G01N 33/52
[52] U.S. Cl. ........................................ 436/172; 424/2; 424/7.1; 436/63; 436/829
[58] Field of Search .......................... 436/63, 172, 829; 424/7.1, 2

[56] References Cited

U.S. PATENT DOCUMENTS 4,343,782  8/1982  Shapiro .................................. 436/63

OTHER PUBLICATIONS

Osmotic Swelling of Phospholipid Vesicles Causes them to Fuse with a Planar Phospholipid Bilayer Membrane, Cohen et al., Science, vol. 217, Jul. 30, 1982, pp. 458-460.

Interaction of Human Erythrocyte Ghosts of Liposomes with Polyethylene Glycol detected by Fluorescene Polarization, pp. 426-431.

Ohno et al., Biochem. and Biophys. Res. Comm., vol. 102 No. 1, Sep. 1981, Owen, Chemical Abstract 93:91333V, 1980.

*Primary Examiner*—Barry S. Richman
*Assistant Examiner*—Robert J. Hill Jr.
*Attorney, Agent, or Firm*—Burgess, Ryan & Wayne

[57] ABSTRACT

This method of measuring membrane fusions between liposomes made of phospholipid is characterized by the combination of ionophores, fluorescent dyes sensitive to the membrane potential (interior negative) and porins which are the pore-forming membrane proteins. By this method, the extent of liposome fusion can be determined easily and accurately.

5 Claims, 7 Drawing Figures

PORIN-LIPOSOME + PORINLESS-LIPOSOME

METHOD OF MEASURING MEMBRANE FUSION

This invention relates to a method of measuring membrane fusions among liposomes made of phospholipids and with or without protein.

Liposomes made of phospholipids, e.g. phosphatidylcholine, have been used as a good model for studying the structure and the function of biological membranes by a number of investigators. Recently, a number of workers characterized liposomes as the potential vehicle for drug delivery. If the liposomes can be fused with cell membranes in vivo, a possible application of drugs containing liposomes for medical use will be unlimited. For example, if the liposomes containing anti-tumor drug(s) in their intraliposomal space can be delivered specifically to tumor cells and be fused with them, the adverse effects caused by the drug can be minimized. Therefore the development of the method that can be used for the research of the mechanism of membrane fusion is urgent. However, the method for measuring the membrane fusion quantitatively is hardly seen, and therefore the knowledge relating to the mechanism of membrane fusion is not well understood. For example, the method of monitoring the fluorescent intensity upon mixing of the internal contents of two fused liposomes had been developed. In this method, the fusion of the liposomes containing terbium ions ($Tb^{3+}$) and the liposomes containing dipicolinic acid (DPA) resulted in an enhancement of fluorescence emission of $Tb(DPA)_3^{3-}$. Because of the intravesicular contents, Tb and DPA leak out from liposomes and external EDTA influx into liposomes during the membrane fusion, this method cannot quantitatively measure the membrane fusion accurately.

It is an object of the invention to provide an accurate and simple method to measure membrane fusion.

The present invention has been achieved by combining the functions of a cation specific ionophore, a membrane potential sensitive fluorescent dye and a porin, a pore-forming membrane protein extracted from *Escherichia coli*.

The principle of the present invention to measure membrane fusion is to fuse liposomes containing porins with the $K^+$-loaded liposomes lacking porin (porinless-liposomes). The unfused porinless-liposomes were quantified by determination of the extent of fluorescence quenching of the fluorescent dye upon dilution of the mixture with a $Na^+$-containing medium in the presence of an ionophore. The porin containing liposomes (porin-liposomes) do not accumulate the fluorescent dye due to the instantaneous equilibrium of $K^+$ and $Na^+$ across the membranes via porin pores.

Many kinds of phospholipids are available for those two types of liposomes. They include phosphatidylcholine, phosphatidylserine, phosphatidylinositol, phosphatidylethanolamine, phosphatidic acid, cardio lipin, sphingomyelin, and the like. Two or more kinds of phospholipids can be mixed to prepare the liposomes. The phospholipids species for two types of liposomes can be the same or different.

Materials other than the phospholipids can be added to the liposomes membranes such as cholesterol for example that alter the physical properties of the membrane.

The pore forming porin unit is composed of three identical subunits. They are purified from the outer membrane of gram-negative bacteria such as *Escherichia coli* and *Salmonella*, and the outer membrane of mitochondria.

The two types of liposomes are usually spherical and their intraliposomal space is filled with an aqueous solution. The internal solution of porinless-liposomes should contain the cation which is specific for the ionophore to be used. Such cations include potassium ion, hydrogen ion, sodium ion, rubidium ion, cesium ion, lithium ion and calcium ion.

The salt of these ions is entrapped in the internal space of liposomes. They may be inorganic salts such as a chloride, nitrate, sulfate, phosphate and carbonate or organic salts such as an acetate, citrate, succinate and gluconate. The salt concentration should be about 20 to 200 mM.

Two types of liposomes can be prepared according to the conventional methods. For example, phospholipids dissolved in an organic solvent such as chloroform or ether are dried to a film in a spitz tube. The dried film of phospholipids is suspended in the above salt solution and sonicated. For the preparation of porin-liposomes, the phospholipid film dried as above is resuspended in distilled water by sonic oscillation and then porins are added. The mixture is dried again at about 45° C. under a nitrogen gas stream and kept in an evacuated desiccator. Then the dried film is resuspended in the above salt solution by sonic oscillation. Porins are transmembraneous proteins that form pores in the membrane.

The membrane fusions between the two types of liposomes can be initiated by adding the fusogens such as calcium ion, polyethylene glycol or Sendai virus or by imposing the electric field. Calcium-induced membrane fusions can be terminated by dilution of the mixture or by addition of chelates such as EDTA or EGTA.

After termination of the membrane fusion, the reaction mixtures are diluted with the $K^+$-free medium containing $Na^+$, the fluorescent dye and the ionophore.

Many kinds of ionophores can be used in the present method. They are valinomycin (ionophore for potassium ion, rubidium ion and cesium ion), gramicidin A (ionophore for hydrogen ion, lithium ion, sodium ion and potassium ion), nonactin, monactin and dicyclohexyl 18-crown-6 (ionophores for potassium ion and sodium ion), cryptate 211 (ionophore for calcium ion, lithium ion and sodium ion), nigericin (ionophore for calcium ion), monensin (ionophore for sodium ion), A23187 and X537A (ionophores for calcium ion) and alamethecin (ionophore for potassium ion). Optimum concentrations of these ionophores vary depending on the kinds of ionophores and the concentrations of cations and two types of liposomes to be used. Therefore, the conditions for each combination of ionophore and ions should be determined in advance.

The fluorescent dyes include cyanine dyes such as 3,3'-dipropylthiodicarbocyanine iodide (diS-$C_3$-(5)), 3,3'-dipropyloxadicarbocyanine iodide (diO-$C_3$-(5)) and 3,3'-dipropylinodotricarbocyanine iodide (diI-$C_5$-(7)); merocyanine dyes such as 5-[3-sodium sulfopropyl-2(3H)-benzoxazolylidene)-2-butenylidene]-1,3-dibutyl-2-thiobarbituric acid (Merocyanine 540), 5-[(1-γ-triethylammonium sulfopropyl-4(1H)-quinolylidene]-3-ethylrhodamine (WW375), 5-[(3-γ-sodium sulfopropyl-2(3H)-thiazolinylidene)-2-butenylidene]-1,3-dibutyl-2-thiobarbituric acid and 5-[(3,3-dimethyl-1-γ-sodium sulfopropyl-2(3H)-indolylidene)-2-butenylidene]-3-ethyl rhodamine, and oxonal dyes such as bis-[1,3-dibutylbarbituric acid-(5)]-pentamethineoxonol (diBA- $C_4$-(5)), bis-[3-phenyl-rhodamine-(5)]methinoxonol and bis-[3-γ-sodium sulfopropyl-rhodamine-(5)]methinoxonol. The suitable concentration of the fluorescent dyes range around $10^{-6}$M.

The ionophores and the fluorescent dyes are dissolved in ethanol, acetone or a similar suitable solvent.

The change of the fluorescence intensity can be monitored by a fluorophotometer. The optimum excitation and emission wave lengths to be used depend on the fluorescent dyes to be employed.

On dilution of the reaction mixture with a solution containing $Na^+$, the ionophore and the fluorescent dye, the fluorescence intensity of the dye decreases and then recovers exponentially. The plots of the logarithms of the differences of the fluorescence intensities from that of equilibrium versus time show a linear line. The extent of the maximum fluorescence quenching representing the ionophore-induced potential of porinless-liposomes can be obtained by extrapolating the line to time 0. As the extent of the fluorescent quenching is a function of the concentration of porinless-liposomes, the decrease of the concentration of porinless-liposomes due to the fusions of the liposomes with porin-liposomes results in the decrease of the quenching of the dye. Accordingly, the degree of membrane fusions can be determined from the extent of fluorescence quenching of the dye.

We explain the principle of the assay by the present method using valinomycin and diS-$C_3$-(5) as the ionophore and the fluorescent dye, respectively.

Upon addition of valinomycin to a solution containing the $K^+$-loaded porinless-liposomes, the potassium ion efluxes from the liposomes because the potassium ion concentration of the medium is lower than that of internal solution. Since the chemical potential of the liposome interior becomes negative, diS-$C_3$-(5), having the positive charge, enters into the liposomes. The fluorescence of the dye in the liposome is quenched. Porin-liposomes do not accumulate diS-$C_3$-(5) due to the instantaneous equilibrium of potassium and sodium ions across the membranes via porin pores. By the fusion of porin-liposomes with $K^+$-loaded porinless-liposomes, loaded potassium ion efluxes immediately through the porin pores. Accordingly, the dye does not accumulate and hence no fluorescence quenching can be measured.

The present method can measure the membrane fusions induced by many kinds of fusogens simply and accurately. Therefore, this invention may contribute to the elucidation of the mechanism of the membrane fusion, to the application of the liposomes for the drug, and to a search of fusogens.

EXAMPLE 1

1.8 mg of phosphatidylserine and 0.45 mg of phosphatidylcholin both in chloroform were mixed in a spitz tube and the solvent was removed under a nitrogen gas stream at room temperature. The tube was placed in an evacuated desiccator containing silica gel for one hour to dry the phospholipid completely.

150 μl distilled water was added to the tube and the phorpholipids film attached to the tube was scraped off by the use of a glass rod. The lipid suspension was subjected to sonic oscillation for 2 minutes using a microtip of Bransonic Sonifier 200. For the preparation of the porin-liposomes, 110 μg porins in distilled water was added to the above suspension. The mixture was dried again at 40° C. under a nitrogen gas stream. The tube was placed in a desiccator as above for about one hour. The dried film was resuspended in 150 μl of 10 mM Tris-HCl buffer (pH 8.0) containing 100 mM potassium gluconate by sonic oscillation for 10 minutes as above. The porin- and porinless-liposomes made by this procedure were about 250 to 500 Å in diameter.

10 μl of the 100 mM potassium gluconate/10 mM Tris-HCl buffer (pH 8.0) containing calcium ion was added to the mixture of 10 μl each of porin-and porinless-liposomes and the reaction mixture was incubated at a fixed temperature.

The reaction was terminated by diluting the reaction mixture with 280 μl of 10 mM potassium gluconate/10 mM Tris-HCl buffer (pH 8.0).

20 μl of the above mixture was added to the mixture of 25 ml of 100 mM sodium gluconate/10 mM Tris-HCl buffer (pH 8.0) and 2 μl of diS-$C_3$-(5) dissolved in ethanol in a cuvette. After a minute, 8 μl of 12 μM valinomycin dissolved in acetone was added to the mixture and mixed quickly. The change of the fluorescence intensity was monitored at 670 nm (slit width was 6 nm) with an excitation wavelength at 620 nm (slit width was 6 nm) using a Hitachi 650-10M fluorescence spectrophotometer.

Figure 1:
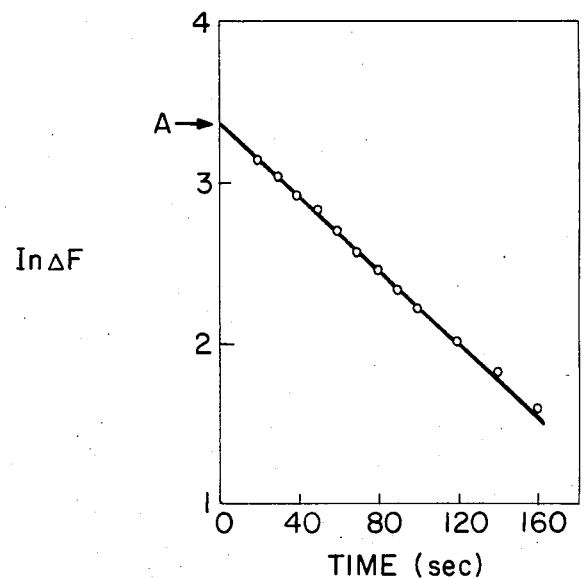
FIG. 1 shows a plot of change in fluorescene intensity versus time.

FIG. 1 shows the time-course of the change of the fluorescence intensity after adding valinomycin. Logarithms of the differences of fluorescence intensities between a time and at equilibrium (ln ΔF) were plotted against time. The maximum fluorescence quenching indicated by the point A in FIG. A can be obtained by extrapolating the line to time 0.

Figure 2:
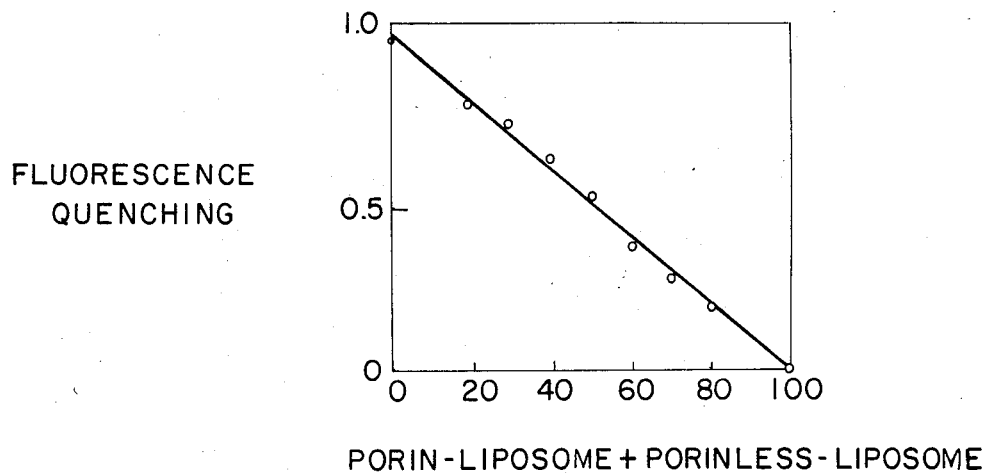
FIG. 2 shows a plot of fluorescence quenching versus quantity of porinless-liposomes.
Figure 3:
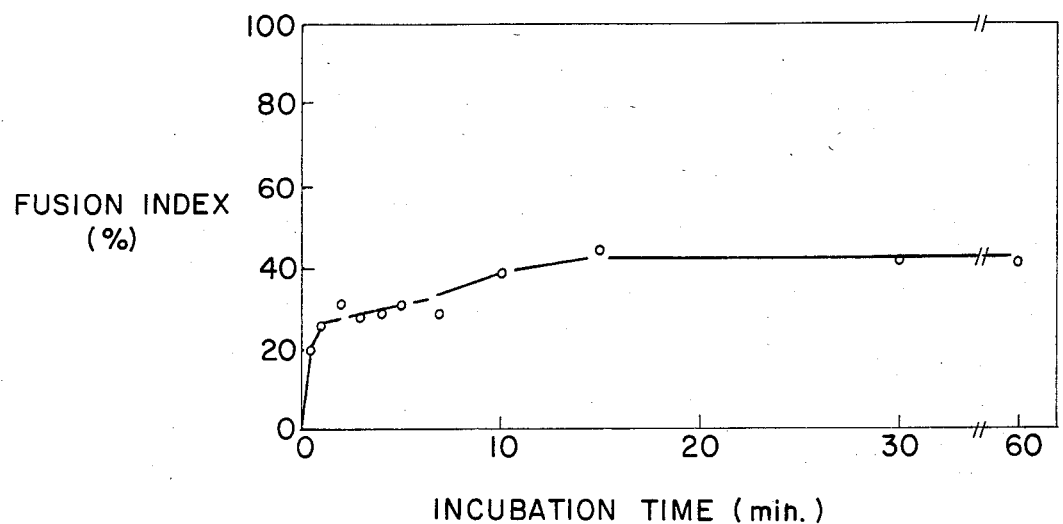
FIG. 3 shows a plot of extent of fusions versus incubation time.

FIG. 2 shows the relationship between the quantity of porin-liposomes and the extent of fluorescence quenching. The porin-liposomes and porinless-liposomes were mixed at various ratios and the fluorescence intensity was recorded as described above. The extent of fluorescence quenching by the porinless-liposomes only was normalized to 1.0. The extent of fluorescence quenching was shown to be linearly related to the population of the porinless-liposomes. The membrane fusions induced by 10 mM $Ca^{++}$ were carried out at room temperature. FIG. 3 shows the time-course of the membrane fusions between two types of liposomes. The extent of the membrane fusion can be expressed by the fusion index computed according to the following equation.

Fusion index (%)=[1-(ΔF/ΔF₀)]×100

ΔF₀: the extent of fluorescence quenching of the dye without a fusogen.

ΔF: the extent of fluorescence quenching of the dye with a fusogen.

Figure 4:
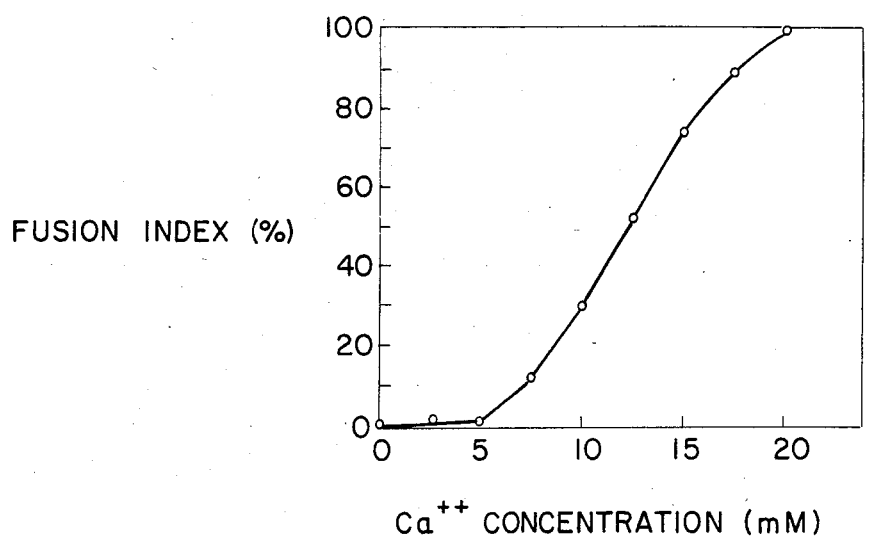
FIG. 4 shows a plot of extent of fusions versus calcium ion concentration.

FIG. 4 shows the effect of calcium ion on the membrane fusions. The reaction mixture was incubated at room temperature for 3 minutes.

Figure 5:
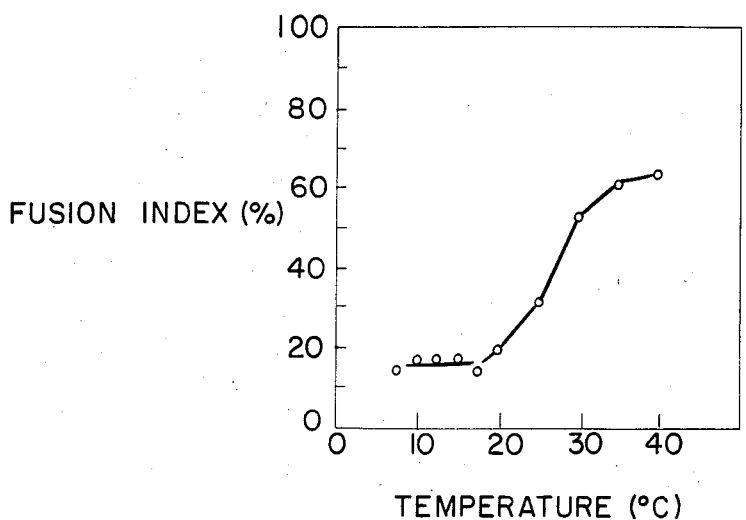
FIG. 5 shows a plot of extent of fusions versus incubation temperature.

FIG. 5 shows the effect of incubation temperature on membrane fusions. The reaction mixture contained 12.5 mM calcium and was incubated for 3 minutes.

EXAMPLE 2

In this example polyethylene glycol 4000 (PEG-4000) was used as a fusogen instead of calcium ion.

Figure 6:
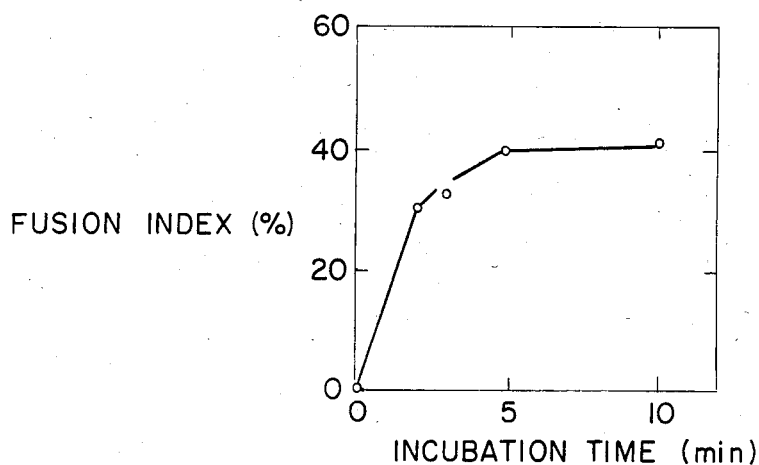
FIG. 6 shows another plot of extent of fusion versus incubation time.

The mixture containing 10 μl each of porin-and porinless-phosphatidylcholine liposomes were mixed with 40 μl of 37.5% w/v of PEG-4000 in 100 mM potassium gluconate/10 mM Tris-HCl buffer (pH 8.0). The mixture was incubated at 35° C. and diluted with 540 μl of the same buffer. Fluorescence intensity was measured as above using 20 μl of the mixture. FIG. 6 shows the time-course of PEG-induce membrane fusions.

Figure 7:
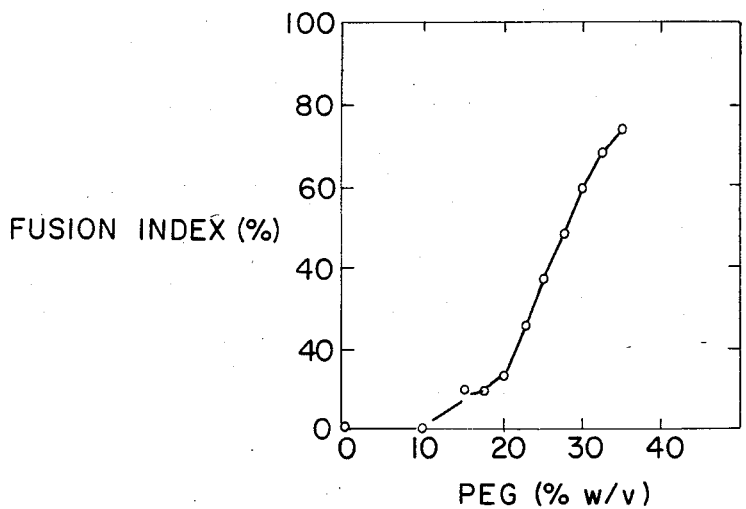
FIG. 7 shows a plot of extent of fusion versus polyethylene glycol concentration.

FIG. 7 shows relationship between the PEG concentration and the extent of membrane fusions. The reaction was carried out at 35° C. for 10 minutes.

We claim:

1. A method of measuring extent of membrane fusions comprising:
   (a) forming an aqueous mixture containing fused liposomes, wherein said fused liposomes are formed by fusing liposomes containing porins with liposomes lacking in porins and loaded with a first cation;
   (b) admixing with the aqueous mixture, a fluorescent dye that is sensitive to negative potential, an ionophore specific for the first cation, and a second cation which does not combine with the ionophore and which is capable of instantaneously equilibrating with the first cation across liposome membranes containing porins; and
   (c) measuring fluorescene quenching of the dye in the mixture formed in step (b) as an indication of the extent of membrane fusions.

2. The method of claim 1 wherein the first cation is at least one cation selected from the group consisting of hydrogen, sodium, potassium, rubidium, cesium, lithium and calcium.

3. The method of claim 1 wherein the aqueous mixture containing fused liposomes is formed by mixing the liposome containing porins with the first cation loaded liposomes lacking porins in an aqueous medium containing a fusogen and reacting the mixture for a time sufficient to form fused liposomes.

4. The method of claim 3 wherein the fusion reaction is terminated before the fluorescence quenching is measured.

5. The method of claim 3 wherein the fluorescent dye is selected from the group consisting of 3,3'-dipropylthiodicarbocyanine iodide (diS-$C_3$-(5)), 3,3'-dipropyloxadicarbocyanine iodide (diO-$C_3$-(5)), 3,3'-dipropylinodotricarbocyanine iodide (diI-$C_5$-(7)), 5-[3-sodium sulfopropyl-2(3H)-benzoxazolylidene)-2-butenylidene]-1,3-dibutyl-2-2-thiobarbituric acid (Merocyanine 540), 5-[(1-γ-triethylammonium sulfopropyl-4(1H)-quinolylidene]-3-ethylrhodamine (WW375), 5-[(3-γ-sodium sulfopropyl-2(3H)-thiazolinylidene)-2-butenylidene]-1,3-dibutyl-2-thiobarbituric acid and 5-[(3,3-dimethyl-1-γ-sodium sulfopropyl-2(3H)-indolylidene)-2-butenylidene]-3-ethyl rhodamine, bis-[1,3-dibutyl-barbituric acid-5(5)]pentamethineoxonol (diBA-$C_4$-(5)),bis-[3-phenyl-rhodamine-(5)]methinoxonol and bis-[3-γ-sodium sulfopropyl-rhodamine-(5)]methinoxonol.

* * * * *